US006942664B1

(12) United States Patent  (10) Patent No.: US 6,942,664 B1
Voor et al.  (45) Date of Patent: Sep. 13, 2005

(54) RAPIDLY ADJUSTABLE THREADED PIN CLAMP

(75) Inventors: Michael J. Voor, Louisville, KY (US); Seid W. Waddell, Lagrange, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 221 days.

(21) Appl. No.: 10/446,311

(22) Filed: May 28, 2003

Related U.S. Application Data

(60) Provisional application No. 60/384,866, filed on May 31, 2002.

(51) Int. Cl.⁷ .............................................. A61B 17/56
(52) U.S. Cl. ..................................................... 606/54
(58) Field of Search .............................. 606/59, 54, 56, 606/61, 72, 69, 70, 71, 96; 24/524, 525, 527

(56) References Cited

U.S. PATENT DOCUMENTS

| | | | |
|---|---|---|---|
| 4,370,982 A | 2/1983 | Reilly | |
| 4,757,809 A | 7/1988 | Koeneman et al. | |
| 5,336,223 A * | 8/1994 | Rogers | 606/61 |
| 5,454,816 A * | 10/1995 | Ashby | 606/96 |
| 5,951,554 A * | 9/1999 | Holmes | 606/61 |
| 5,976,134 A | 11/1999 | Huebner | |
| 6,080,153 A | 6/2000 | Mata et al. | |
| 6,159,210 A | 12/2000 | Voor | |
| 6,162,223 A | 12/2000 | Orsak et al. | |
| 6,245,071 B1 | 6/2001 | Pierson | |
| 6,355,039 B1 * | 3/2002 | Troussel et al. | 606/61 |
| 6,533,785 B1 | 3/2003 | Frigg et al. | |
| 2002/0169451 A1 * | 11/2002 | Yeh | 606/61 |
| 2003/0153910 A1 * | 8/2003 | Janowski et al. | 606/56 |
| 2003/0216742 A1 * | 11/2003 | Wetzler et al. | 606/96 |

* cited by examiner

Primary Examiner—Eduardo C. Robert
Assistant Examiner—Michael J. Araj
(74) Attorney, Agent, or Firm—Stites & Harbison, PLLC; David W. Nagle, Jr.

(57) ABSTRACT

A clamp for the rapid and accurate positioning of a threaded fixation pin has a central body defining a channel therethrough for receiving a fixation pin. The clamp also includes a locking member with a lower surface adapted to engage and mate with the threads of the fixation pin. Thus, the fixation pin can be rapidly inserted into the desired bone structure by rotating the fixation pin, and as the fixation pin is rotated, it also advances forward due to the engagement of the threads of the fixation pin with the locking member of the clamp. If the forward advance caused by the engagement of the threads of the fixation pin with the locking member can not keep pace with the cutting action, the resultant resistance to insertion in the form of a rearward directed force will cause the locking member to rise up and disengage the threads of the fixation pin.

12 Claims, 6 Drawing Sheets

RAPIDLY ADJUSTABLE THREADED PIN CLAMP

CROSS-REFERENCE TO RELATED APPLICATIONS

The present application claims priority to U.S. Provisional Application Ser. No. 60/384,866 filed May 31, 2002, the entire disclosure of which is incorporated herein by reference.

BACKGROUND OF THE INVENTION

The present invention relates to fixation pins for attaching a frame or immobilizing device to a bone structure of a patient with a skeletal injury, and, more particularly to a clamp for the rapid and accurate positioning of such fixation pins.

In cases of skeletal injuries, such as broken bones and cervical spinal injuries, it is often necessary to fix or stabilize the position of the bones while the injury heals. For example, such fixation may require the attachment of an external frame to long bones or the attachment of a halo orthosis to the skull of a patient. To attach such a frame or immobilizing device to a bone structure, fixation pins are commonly used. A common fixation pin comprises a threaded cylindrical body, a conical tip at the distal end of the cylindrical body for penetrating into a bone, and a head portion at the opposite end of the cylindrical body that is coupled to a means for rotating the fixation pin. Furthermore, in some constructions, a fixation pin has threads for engaging the bone itself, such as a fixation pin used for external fracture fixation. In any event, in a simple configuration, a first set of fixation pins is inserted percutaneously into a bone on a distal side of the fracture, and a second set of fixation pins is inserted percutaneously into a bone on a proximal side of the fracture.

Once the various fixation pins have been appropriately positioned and inserted in this manner, the fixation pins connected to a frame or similar immobilizing device through the use of pin clamps. Specifically, each fixation pin commonly includes a substantially smooth surface. A pin clamp is secured to the frame or similar immobilizing device and engages this substantially smooth surface of the fixation pin to grip and secure the fixation pin. In this regard, prior art pin clamps generally comprise a pair of opposing and facing clamping portions that collectively define one or more channels for receiving and retaining a fixation pin. These opposing and facing clamping portions are adjustably secured relative to one another by screws or similar fasteners. By tightening the screws or similar fasteners, the clamping portions are moved toward one another such that a fixation pin can be gripped and secured in one of the channels defined by the clamping portions. In this manner, the frame or immobilizing device to which the fixation pins are secured prevents or controls the movement of the bone near the fracture.

For further reference, various examples of prior art fixation pins and their uses are referenced and discussed in U.S. Pat. No. 6,159,210 issued to Voor, one of the present applicants. For such discussion and examples of prior art fixation pins and their uses, U.S. Pat. No. 6,159,210 is incorporated herein by reference.

Moreover, the above-referenced '210 patent describes an improved fixation pin. Specifically, the '210 patent describes and claims a fixation pin comprising a body with threads provided along a portion of its length, a cylindrical post coaxially secured to the leading end of the body, a rotary cutting tip formed in the face of the post, and a radial shoulder formed along the boundary of the body and the post. During insertion of this fixation pin, the pin is rotated, and the rotary cutting tip is advanced into the bone. The rotary cutting tip thus cuts a clean cylindrical hole into the bone without requiring a large axial force, while the radial shoulder limits the depth of penetration of the post into the bone. After insertion, the cylindrical post fits snugly in the hole, and no axial force is necessary to hold the fixation pin in place. The described fixation pin can thus be inserted and retained in the bone with a minimal axial force and with little damage to the surrounding bone and tissue. Furthermore, the construction of the fixation pin minimizes the possibly of loosening due to repetitive transverse loading.

Nevertheless, in prior art systems and methods, it remains common for fixation pins, regardless of their particular construction, to be inserted percutaneously into a bone before the complete assembly of the frame or similar immobilizing device. In other words, only after the pins have been appropriately positioned are the pin clamps used to engage the fixation pins and secure the fixation pins to the frame or similar immobilizing device. This sometime creates difficulties in ensuring proper pin positioning and also hinders the ability to tighten or otherwise adjust a fixation pin after placement and assembly of the frame or similar immobilizing device.

It is therefore an object of the present invention to provide a clamp that allows for rapid and accurate placement of a threaded fixation pin.

It is a further object of the present invention to provide a clamp that allows for fine adjustment of a threaded fixation pin after placement.

It is yet a further object of the present invention to provide a clamp that allows for temporary placement of a threaded fixation pin, thus allowing for assembly of a frame or immobilizing device without commitment to final pin positions.

These and other objects and advantages of the present invention will become readily apparent and addressed through a reading of the discussion below and appended drawings.

SUMMARY OF THE INVENTION

The present invention is a clamp for the rapid and accurate positioning of threaded fixation pins used for attaching a frame or immobilizing device to a bone structure. A preferred clamp made in accordance with the present invention has a central body defining a channel therethrough for receiving a fixation pin. In use, the preferred clamp is mounted or otherwise fixed in space relative to the bone into which the fixation pin is to be inserted. The fixation pin is inserted into and pushed forward through the channel defined through the central body of the clamp until the rotary cutting tip of the fixation pin is in contact with the patient.

The preferred clamp also includes a locking member with a lower surface adapted to engage and mate with the threads of the fixation pin. This locking member is secured relative to the interior of the clamp by a leaf spring which biases the locking member into engagement with the fixation pin, but which allows for some vertical movement of the locking member relative to the fixation pin.

With the fixation pin received in the preferred clamp, the fixation pin can then be rapidly inserted into the desired bone structure by rotating the fixation pin. Specifically, as the fixation pin is rotated, it also advances forward due to the engagement of the threads of the fixation pin with the locking member of the clamp. With such rotation and forward advance of the fixation pin, the rotary cutting tip of the fixation pin engages and cuts into the bone. However, if the forward advance caused by the engagement of the threads of the fixation pin with the locking member can not keep pace with the cutting action, the resultant resistance to insertion in the form of a rearward directed force will cause the locking member to rise up and disengage the threads of the fixation pin, allowing the rotation of the fixation pin to continue without any forward advance. Thus, the clamp of the present invention allows the cutting action to continue independent of the forward advance of the fixation pin.

DETAILED DESCRIPTION OF THE INVENTION

Figure 1:
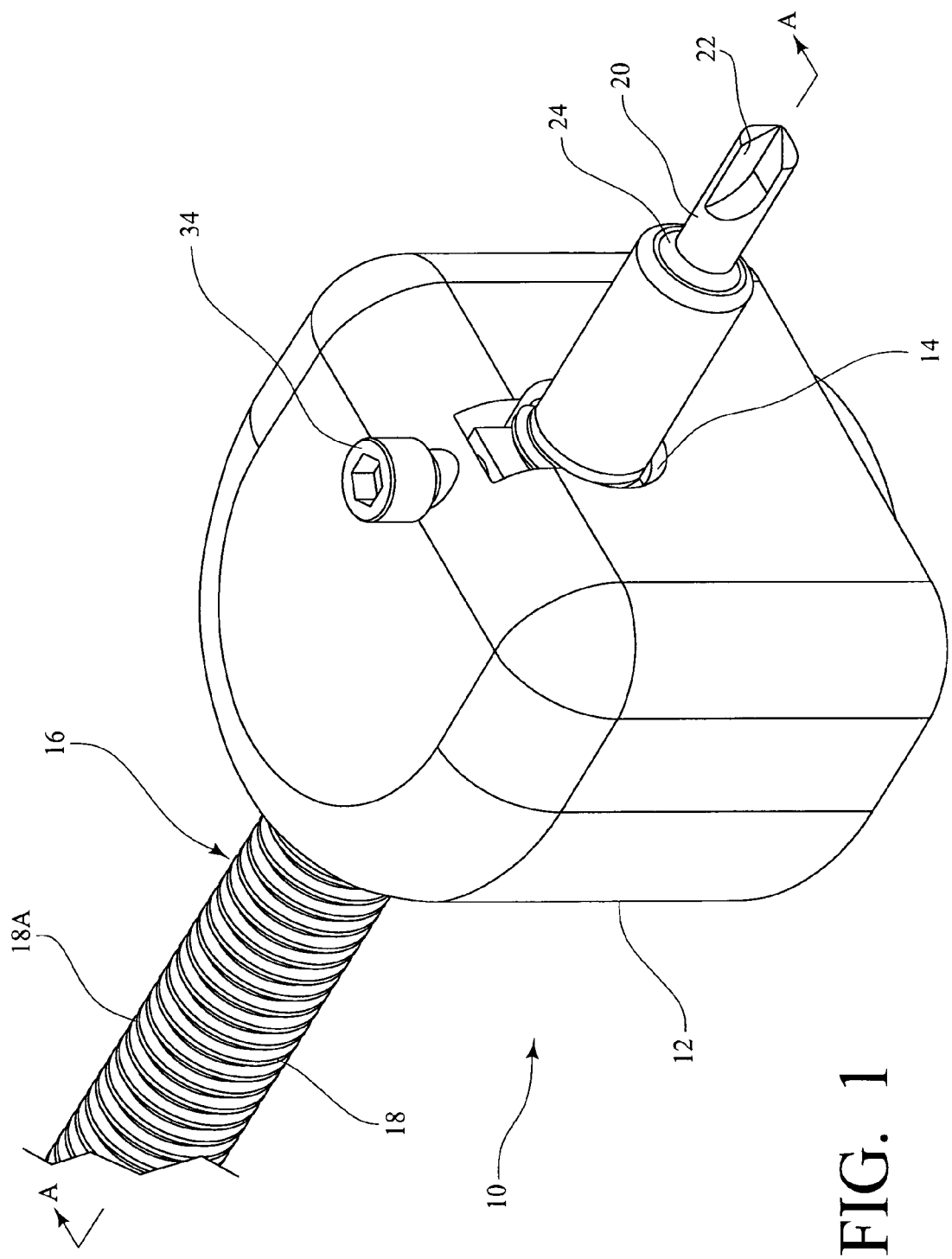
FIG. 1 is a perspective view of a threaded pin clamp made in accordance with the present invention.

The present invention is a clamp for the rapid and accurate positioning of threaded fixation pins used for attaching a frame or immobilizing device to a bone structure. FIGS. 1–4 provide various perspective and sectional views of a preferred clamp 10 made in accordance with the present invention.

As shown in FIGS. 1–4, the preferred clamp 10 has a central body 12 defining a channel therethrough 14 for receiving a fixation pin 16. In this regard, as described in the '210 patent referenced above, the fixation pin 16 preferably comprises a body 18 with threads 18a provided along a portion of its length, a cylindrical post 20 coaxially secured to (and, in this preferred embodiment, integral with) the leading end of the body 18, a rotary cutting tip 22 formed in the face of the post 20, and a radial shoulder 24 formed along the boundary of the body 18 and the post 20. Nevertheless, it is contemplated that other threaded fixation pins could be positioned using the preferred clamp 10 without departing from the spirit and scope of the present invention.

In use, the preferred clamp 10 is mounted or otherwise fixed in space relative to the bone into which the fixation pin 16 is to be inserted. The fixation pin 16 is inserted into and pushed forward through the channel 14 defined through the central body 12 of the clamp 10 until the rotary cutting tip 22 is in contact with the patient. In other words, the fixation pin 16 is loaded into the preferred clamp 10 before any percutaneous insertion of the pin into a bone.

Figure 2:
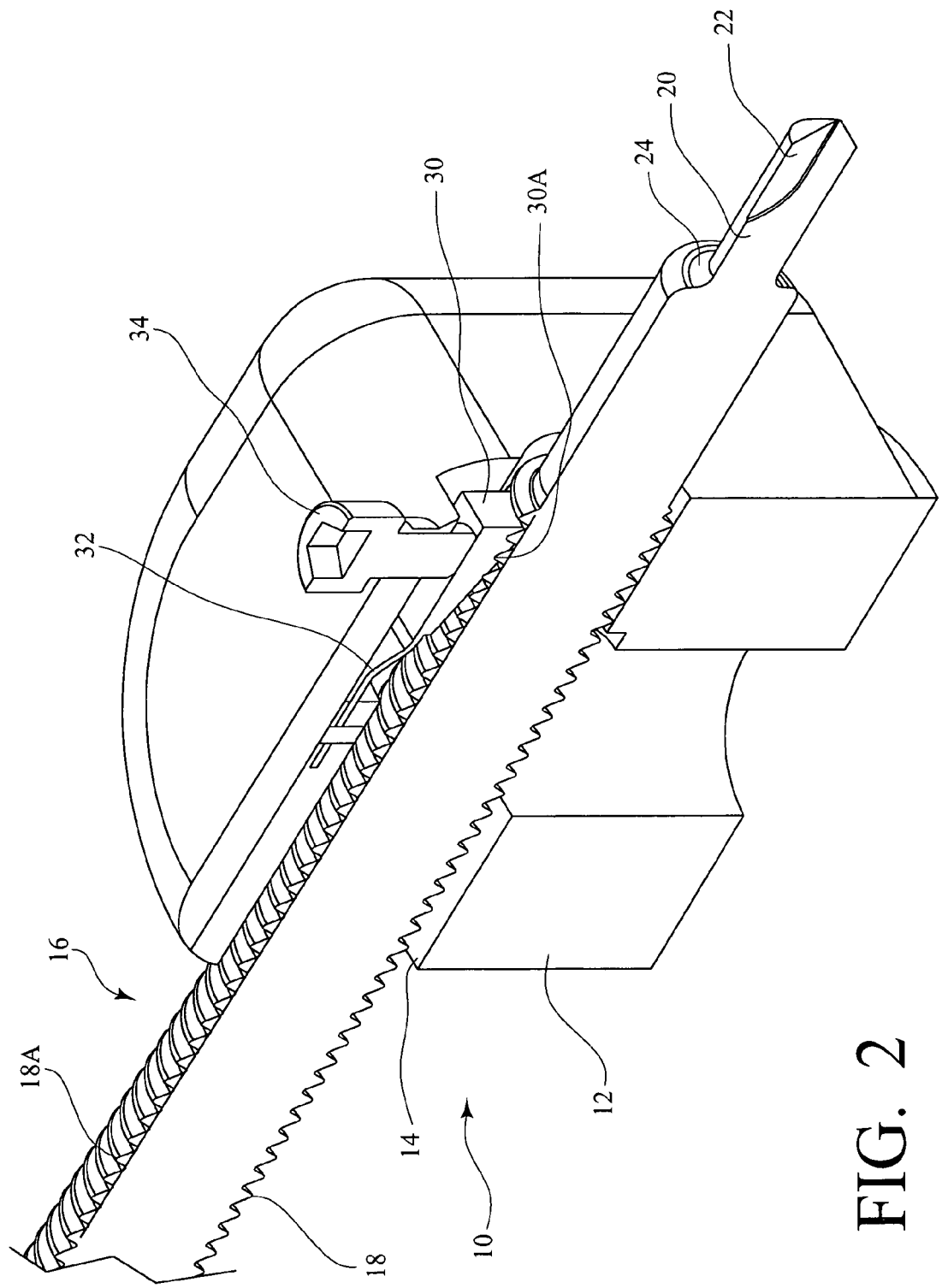
FIG. 2 is a perspective sectional view of the threaded pin clamp of FIG. 1, taken along line A—A of FIG. 1.
Figure 3:
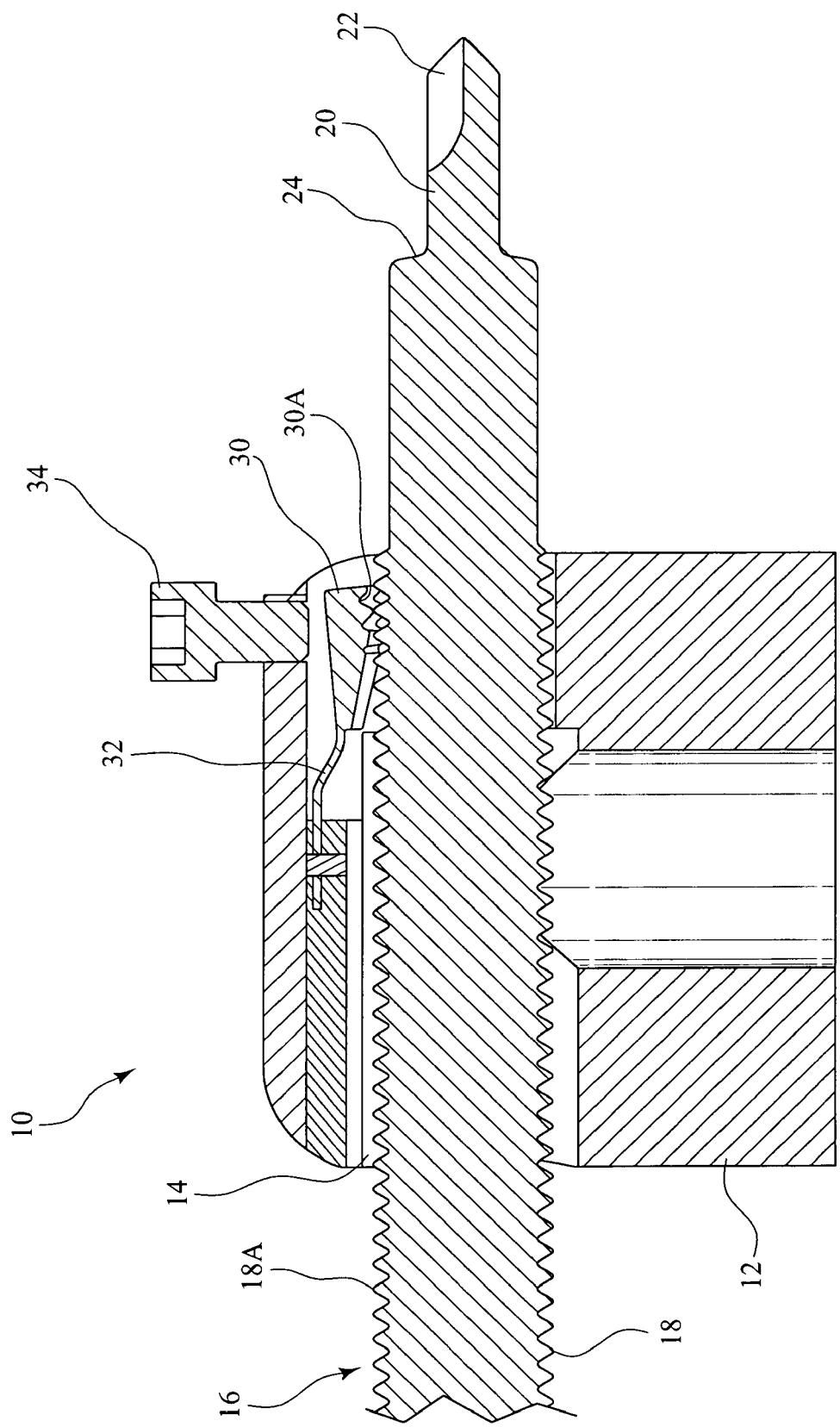
FIG. 3 is a sectional view of the threaded pin clamp of FIG. 1, taken along line A—A of FIG. 1, in which the locking member is in an unlocked position.
Figure 4:
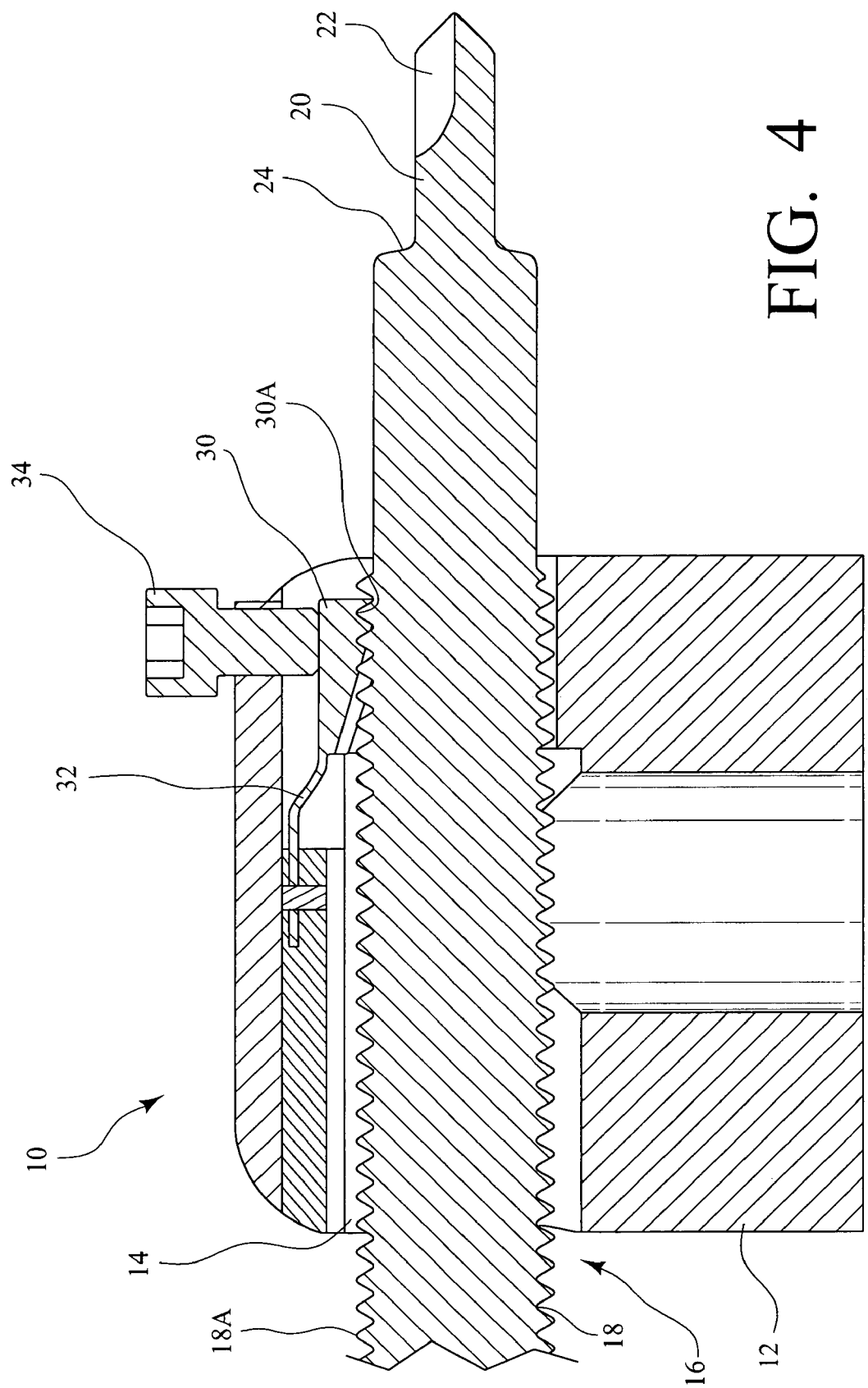
FIG. 4 is a sectional view of the threaded pin clamp of FIG. 1, taken along line A—A of FIG. 1, in which the locking member is in a locked position.

As best shown in FIGS. 2–4, the clamp 10 includes a locking member 30 with a lower surface 30a adapted to engage and mate with the threads 18a of the fixation pin 16. This locking member 30 is secured relative to the interior of the clamp 10 by a leaf spring 32 (or similar biasing means) which biases the locking member 30 into engagement with the fixation pin 16, but which allows for some vertical movement of the locking member 30 relative to the fixation pin 16. Thus, the locking member 30 does not unduly hinder the forward advance of the fixation pin 16 as it is manually loaded into the clamp 16.

With the fixation pin 16 received in the preferred clamp 10, the fixation pin 16 can then be rapidly inserted into the desired bone structure. Specifically, the head portion (not shown) of the fixation pin 16 is coupled to a means for rotating the fixation pin 16. For example, in its simplest form, the means for rotating the fixation pin 16 could be a screwdriver, or a drill or similar mechanical device could provide for the desired rotation. In any event, as the fixation pin 16 is rotated, it also advances forward due to the engagement of the threads 18a of the fixation pin 16 with the locking member 30 of the clamp 10. With such rotation and forward advance of the fixation pin 16, the rotary cutting tip 22 engages and cuts into the bone. However, if the forward advance caused by the engagement of the threads 18a of the fixation pin 16 with the locking member 30 can not keep pace with the cutting action (e.g., if the fixation pin 16 is rotated at a high speed), the resultant resistance to insertion in the form of a rearward directed force will cause the locking member 30 to rise up and disengage the threads 18a of the fixation pin 16, allowing the rotation of the fixation pin 16 to continue without any forward advance. In other words, the locking member 30 is essentially pushed way from the fixation pin 16. Thus, the clamp 10 of the present invention allows the cutting action to continue independent of the forward advance of the fixation pin 16.

Furthermore, because the leaf spring 32 biases the locking member 30 into engagement with the fixation pin 16, when rotation of the fixation pin 16 is stopped, the engagement of the threads 18a of the fixation pin 16 with the locking member 30 of the clamp 10 ensures that the fixation pin 16 is held firmly in place.

As a further refinement, and as illustrated in FIGS. 1–4, the preferred clamp 10 also includes a set screw 34 that is threaded through an opening defined through the upper surface of the clamp 10. In a first or "unlocked" position (as shown in FIG. 3), the set screw 34 does not contact the locking member 30. However, in a second or "locked" position (as shown in FIG. 4), the set screw 34 does contact the locking member 30, pressing it downwardly and forcing it to engage and mate with the threads 18a of the fixation pin 16. In such a locked position, and in the absence of any rotation of the fixation pin 16, movement of the fixation pin 16 relative to the clamp 10 is prevented. For example, the set screw 34 can be set to the locked position once the position of the fixation pin 16 has been finalized.

Figure 5:
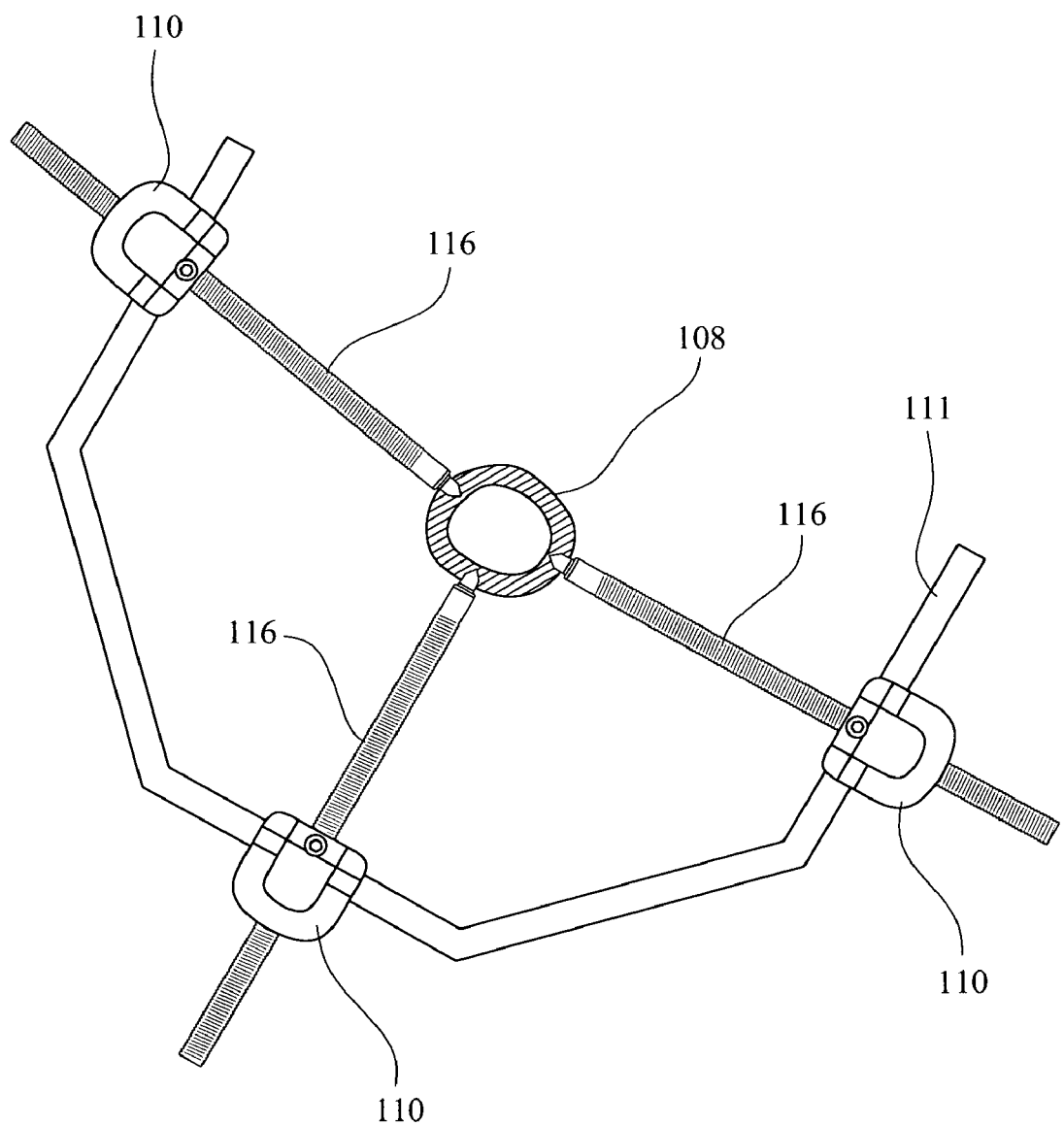
FIG. 5 is a plan view of a plurality of threaded pin clamps made in accordance with the present invention being used for stabilization of a spinal or similar bone injury.

For an example of the use of a preferred clamp of the present invention, FIG. 5 is plan view of a plurality of threaded pin clamps 110 made in accordance with the present invention being used for stabilization of a spinal or similar bone injury. As shown, the generally C-shaped frame 111 has three associated clamps 110, each of said clamps receiving and retaining a respective fixation pin 116. Each of these fixation pins 116 has been inserted and advanced through a clamp 110 and into the bone 108, thus allowing the frame 111 to prevent or control movement of the bone 108.

Figure 6:
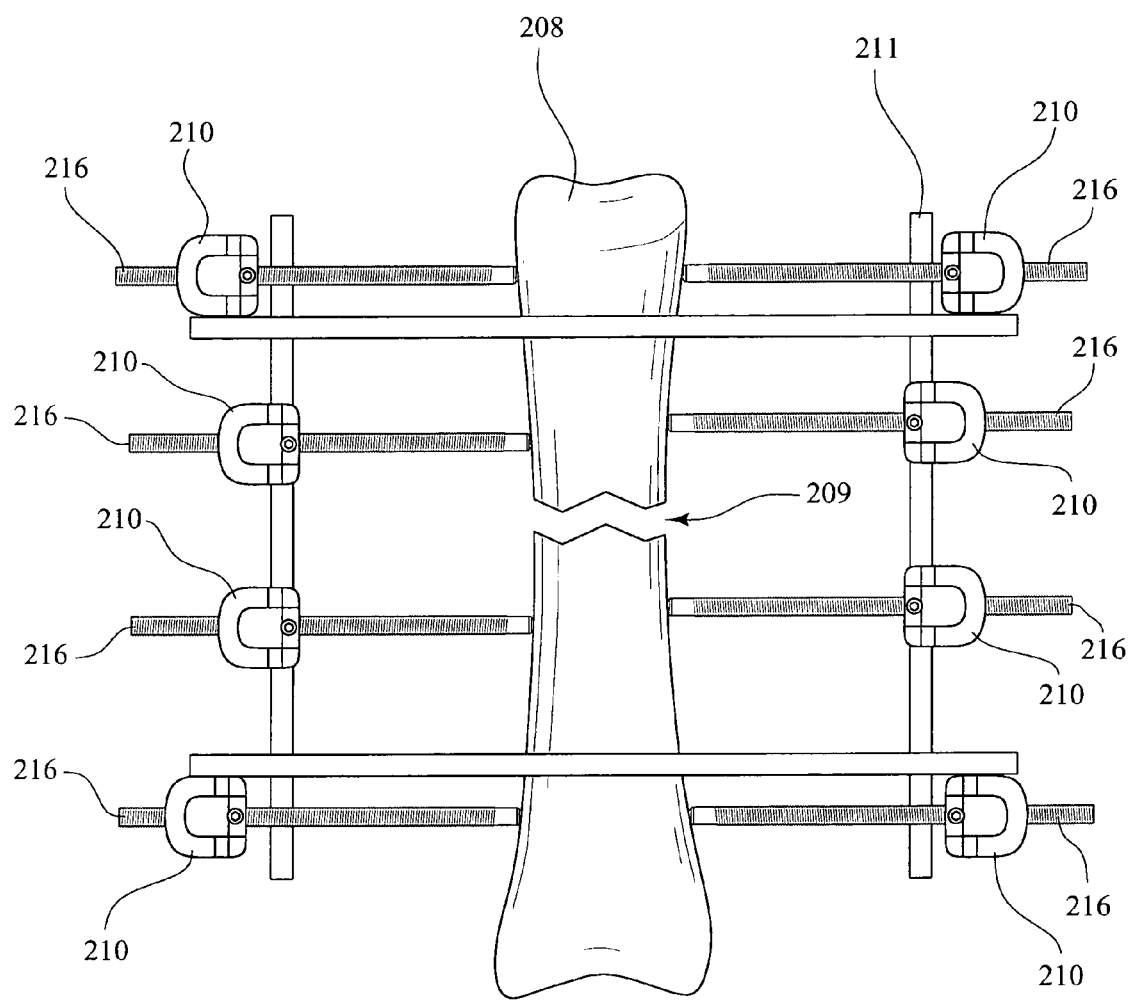
FIG. 6 is a side view of a plurality of threaded pin clamps made in accordance with the present invention being used for stabilization of a long bone fracture.

For another example of the use of a preferred clamp of the present invention, FIG. 6 is a side view of a plurality of threaded pin clamps 210 made in accordance with the present invention being used for stabilization of a long bone fracture. In this example, the frame 211 has eight associated clamps 210, four on each side of a fracture 209 through the bone 208. Each these clamps 210 receives and retains a respective fixation pin 216, and each of these fixation pins 216 has been inserted and advanced through a clamp 210 and into the bone 208, thus allowing the frame 211 to prevent or control movement of the bone 208 in the region of the fracture 209.

It will be obvious to those skilled in the art that further modifications may be made to the embodiments described herein without departing from the spirit and scope of the present invention.

What is claimed is:

1. A clamp for a fixation pin, comprising:
    a central body defining a channel therethrough for receiving said fixation pin, said fixation pin being provided with threads along a portion of its length and including a cutting tip; and
    a locking member depending from said central body and adapted to selectively engage the threads of said fixation pin, such that, when said fixation pin is rotated to initiate a cutting action, engagement of said locking member with the threads of said fixation pin causes the fixation pin to advance forward.

2. The clamp as recited in claim 1, and further comprising a biasing means that secures said locking member to said central body and biases said locking member into engagement with the threads of said fixation pin.

3. The clamp as recited in claim 2, wherein said biasing means is a leaf spring.

4. The clamp as recited in claim 1, and further comprising a set screw threaded through an opening defined through the central body of the clamp, wherein in a first position, said set screw does not contact said locking member, but in a second position, said set screw contacts said locking member, pressing it into engagement with the threads of said fixation pin.

5. An apparatus for attaching an immobilizing device to a bone structure, comprising:
    a fixation pin provided with threads along a portion of its length and including a cutting tip, said fixation pin being adapted for insertion into said bone structure; and
    a clamp adapted to be secured to said immobilizing device and defining a channel therethrough for receiving said fixation pin, said clamp including a locking member adapted to selectively engage the threads of said fixation pin;
    wherein, when said fixation pin is rotated to initiate a cutting action, engagement of said locking member with the threads of said fixation pin causes the cutting tip of said fixation pin to advance forward into the bone structure, but disengagement of said locking member allows rotation of said fixation pin to continue without any such forward advance.

6. The apparatus as recited in claim 5, wherein said clamp further includes a biasing means that secures said locking member to said clamp and biases said locking member into engagement with the threads of said fixation pin.

7. The apparatus as recited in claim 6, wherein said biasing means is a leaf spring.

8. The apparatus as recited in claim 5, wherein said clamp further includes a set screw threaded through an opening defined through the clamp, wherein in a first position, said set screw does not contact said locking member, but in a second position, said set screw contacts said locking member, pressing it into engagement with the threads of said fixation pin.

9. A clamp for a fixation pin, comprising:
    a central body defining a channel therethrough for receiving said fixation pin, said fixation pin being having a tip for performing a cutting action when said fixation pin is rotated; and
    a locking member depending from said central body, including
        a surface adapted to engage said fixation pin, and when so engaged to said fixation pin, causing said fixation pin to advance forward when rotated, and
        a biasing means for urging the surface of said locking member into engagement with said fixation pin until a resultant resistance to the forward advance of said fixation pin during the cutting action causes disengagement.

10. The clamp as recited in claim 9, wherein said biasing means is a leaf spring.

11. The clamp as recited in claim 9, wherein said clamp further includes a set screw threaded through an opening defined through the central body of said clamp, wherein in a first position, said set screw does not contact said locking member, but in a second position, said set screw contacts said locking member, pressing it into engagement with said fixation pin.

12. An apparatus for attaching an immobilizing device to a bone structure, comprising:
    a plurality of clamps secured to said immobilizing device at predetermined locations relative to said bone structure; and
    a plurality of fixation pins, each fixation pin being provided with threads along a portion of its length and including a cutting tip, each fixation pin being adapted for insertion into said bone structure, and each fixation pin being received and retained in a respective clamp;
    wherein each clamp includes a locking member adapted to selectively engage the threads of said fixation pin, such that, when each fixation pin is rotated to initiate a cutting action, engagement of said locking member with the threads of said fixation pin causes the cutting tip of said fixation pin to advance forward into the bone structure.

* * * * *